United States Patent
Feller et al.

(10) Patent No.: US 11,428,699 B2
(45) Date of Patent: Aug. 30, 2022

(54) BIOSENSORS INCLUDING SURFACE RESONANCE SPECTROSCOPY AND SEMICONDUCTOR DEVICES

(71) Applicant: INTERNATIONAL BUSINESS MACHINES CORPORATION, Armonk, NY (US)

(72) Inventors: Bobby E. Feller, Los Gatos, CA (US); Jianqiang Lin, Cambridge, MA (US); Robert D. Miller, San Jose, CA (US); Ramachandran Muralidhar, Mahopac, NY (US); Tak H. Ning, Yorktown Heights, NY (US); Sufi Zafar, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 574 days.

(21) Appl. No.: 16/398,954

(22) Filed: Apr. 30, 2019

(65) Prior Publication Data
US 2019/0257843 A1     Aug. 22, 2019

Related U.S. Application Data

(60) Continuation of application No. 15/497,991, filed on Apr. 26, 2017, now Pat. No. 10,345,317, which is a
(Continued)

(51) Int. Cl.
*G01N 33/84*     (2006.01)
*G01N 27/414*     (2006.01)
(Continued)

(52) U.S. Cl.
CPC .......... *G01N 33/84* (2013.01); *G01N 21/553* (2013.01); *G01N 27/4145* (2013.01); *G01N 33/5438* (2013.01); *G01N 33/54373* (2013.01)

(58) Field of Classification Search
CPC .. G01N 33/84; G01N 21/553; G01N 27/4145; G01N 33/54373; G01N 33/5438
See application file for complete search history.

(56) References Cited

U.S. PATENT DOCUMENTS

| 7,923,240 B2 | 4/2011 | Su |
| 8,323,982 B2 | 12/2012 | LeBoeuf et al. |

(Continued)

OTHER PUBLICATIONS

List of IBM Patents or Patent Applications Treated as Related dated Apr. 30, 2019, 2 pages.
(Continued)

*Primary Examiner* — Brian J. Sines
(74) *Attorney, Agent, or Firm* — Tutunjian & Bitetto, P.C.; Kristofer Haggerty (57) ABSTRACT

A sensor including a surface plasmon resonance detector with a reservoir for containing a liquid sample. The sensor further includes a sensing metallic film positioned within the reservoir so that at least a majority of a surface of the sensing metallic film is to be in contact with the liquid sample being housed within the reservoir. The sensory also includes a semiconductor device having a contact in electrical communication with the sensing metal containing film that is positioned within the reservoir. The semiconductor device measures the net charges of molecules within the liquid sample within a Debye length from the sensing metallic film.

20 Claims, 8 Drawing Sheets

Related U.S. Application Data division of application No. 14/328,291, filed on Jul. 10, 2014, now Pat. No. 9,714,952.

(51) Int. Cl.
*G01N 33/543* (2006.01)
*G01N 21/552* (2014.01)

(56) References Cited

U.S. PATENT DOCUMENTS

| | | | |
|---|---|---|---|
| 8,344,750 | B2 | 1/2013 | Blumberg |
| 10,345,317 | B2* | 7/2019 | Feller .................... G01N 33/84 |
| 2003/0186262 | A1 | 10/2003 | Cailloux |
| 2010/0053624 | A1 | 3/2010 | Yoo et al. |
| 2016/0001249 | A1* | 1/2016 | Light .................... C12Q 1/6806 506/26 |
| 2016/0153932 | A1* | 6/2016 | Eklund ................ G01N 27/414 257/253 |
| 2017/0146483 | A1 | 5/2017 | Javey et al. |

OTHER PUBLICATIONS

Aihara, T., et al. "Monolithic Integration of Surface Plasmon Detector and Metal-Oxide-Semiconductor Field-Effect Transistors." IEEE Photonics Journal, Aug. 2013, vol. 5 No. 4. (10 Pages).

Chen. C., et al. "Extended Base H+-Ion Sensitive Bipolar Junction Transistor with SnO2/ITO Glass Sensing Membrane." IEEE Sensors 2009 Conference, Oct. 2009. (pp. 1113-1116).

Chen, W., et al. "Improved DNA Detection By Utilizing Electrically Neutral DNA Probe in Field-Effect Transistor Measurements as Evidenced by Surface Plasmon Resonance Imaging." Biosensors and Bioelectronics Journal, vol. 41, Oct. 2012. (pp. 795-801).

Shevchenko, Y., et al. "In Situ Biosensing with a Surface Plasmon Resonance Fiber Grating Aptasensor." Analytical Chemistry, Aug. 2011. (pp. 7027-7034).

Vanwiggeren, G. "A Novel Optical Method Providing for High-Sensitivity and High-Throughput Biomolecular Interaction Analysis." Sensors and Actuators B: Chemical Journal, vol. 127, Issue 2, Nov. 2007. (pp. 341-349).

Non-Final Office Action issued in corresponding U.S. Appl. No. 16/399,097 dated Nov. 9, 2021, 20 pgs.

\* cited by examiner

BIOSENSORS INCLUDING SURFACE RESONANCE SPECTROSCOPY AND SEMICONDUCTOR DEVICES

BACKGROUND

Technical Field

The present disclosure relates generally to sensors for biomolecule sensing, and more particularly to structures and methods for making measurements from a liquid solution including biomolecules.

Description of the Related Art

Bio-molecule sensing is important in healthcare. One example of bio-molecule sensing is referred to as surface plasmon resonance spectroscopy, generally designated as SPR (surface plasmon resonance). This method is based upon the optical excitation of surface plasmons in thin metal layers. The resonance conditions for the excitation of surface plasmons strongly depend on the optical properties of the dielectrics surrounding the metal layer. Hence, it is principally feasible to determine the refractive index and the layer thickness of thin dielectric layers with high precision. SPR-spectroscopy finds an increasing application in biochemical analysis, since it permits a direct analysis of the interactions between the bio-molecules (for example, antibody/antigen reactions at or near the sensor surface). To this end a reactant (ligand) is immobilized on the metal surface, and the other reactant (analyte) in solution is passed over the surface. The interaction can be directly detected as a change in dielectric constant (refractive index) which can be translated into an increase in layer thickness. There is no marking of the reactants necessary as, for example, with the radioimmunoassay (RIA) or the enzyme-linked immunosorbent assay (ELISA). A drawback that is common to SPR is false positives.

SUMMARY

In one aspect, a sensor is provided that includes a surface plasmon resonance detector with a reservoir for containing a liquid sample, and a sensing metallic film positioned within the reservoir so that at least a majority of a surface of the sensing metallic film is to be in contact with the liquid sample being housed within the reservoir. The sensor further includes a semiconductor device having a contact in electrical communication with the sensing metal containing film that is positioned within the reservoir. The semiconductor device measures the net charges within the liquid sample within a Debye length from the sensing metallic film.

In another aspect, a sensor is provided that includes a bipolar junction transistor that includes an emitter region, a base region and a collector region; and a reservoir for housing a liquid solution. The sensor further includes a metal containing contact that extends from the base region into the reservoir. The metal containing contact provides a sensing surface for measuring at least one of a presence of biomolecules in a solution and temperature of biomolecules in the solution.

In yet another aspect, a method of measuring a concentration of ions in a solution is provided that includes providing electrical communication between a base region of a bipolar junction transistor (BJT) and the solution of ions being measured. The electrical communication between the BJT and the solution of ion being measured is through an extension of a metal containing contact from the base region of the BJT to the solution of ions, in which portion of the metal containing contact immersed in the solution of ions provides a sensing surface. Current is measured from a collector region of the BJT, wherein changes in current being measured from the collector denotes changes in concentration of ions in the solution of ions.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Detailed embodiments of the claimed structures and methods are disclosed herein; however, it is to be understood that the disclosed embodiments are merely illustrative of the claimed structures and methods that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure. For purposes of the description hereinafter, the terms "upper", "lower", "right", "left", "vertical", "horizontal", "top", "bottom", and derivatives thereof shall relate to the embodiments of the disclosure, as it is oriented in the drawing figures. The term "positioned on" means that a first element, such as a first structure, is present on a second element, such as a second structure, wherein intervening elements, such as an interface structure, e.g. interface layer, may be present between the first element and the second element. The term "direct contact" means that a first element, such as a first structure, and a second element, such as a second structure, are connected without any intermediary conducting, insulating or semiconductor layers at the interface of the two elements.

In some embodiments, the methods and structures disclosed herein provide a biomolecule sensor provided by a bipolar junction transistor (BJT). A sensor is disclosed herein that provides for label free detection, i.e., there is no fluorescence or radioactive tag needed to be attached to the target molecule before it can be detected, of bio-molecules. The term "bipolar junction transistor" denotes a type of transistor made of three regions of semiconductor materials each having an inherent electrical charge, i.e., conductivity, such as n-type or p-type conductivity. Each region has been treated, e.g., doped, so that the layer in the middle (called the base region) has a first conductivity type, while the layers around it, i.e., the emitter region and the collector region) have a second conductivity type opposite to the first conductivity type. A bipolar junction transistor with an n-type base is designated PNP, and one with a p-type base is designated NPN. When subjected to current flow, the base acts like a gate, enhancing or inhibiting the current flow from the emitter to the collector. The bio-molecule sensor of the present disclosure also includes a reservoir for housing the liquid solution from which at least a concentration of molecules, e.g., ions, is measured. A sensing surface is immersed in the liquid solution and is in electrical communication with the base region of the BJT. For example, at least 75% of the sensing element is in contact with the liquid solution that is within the reservoir. In some embodiments, the sensing surface is in electrical contact through an electrically conductive extension from the base region. The methods and structures of the present disclosure directed to the bio-molecule sensor composed of a BJT are now described in more detail with reference to FIGS. 1-10.

Figure 1A:
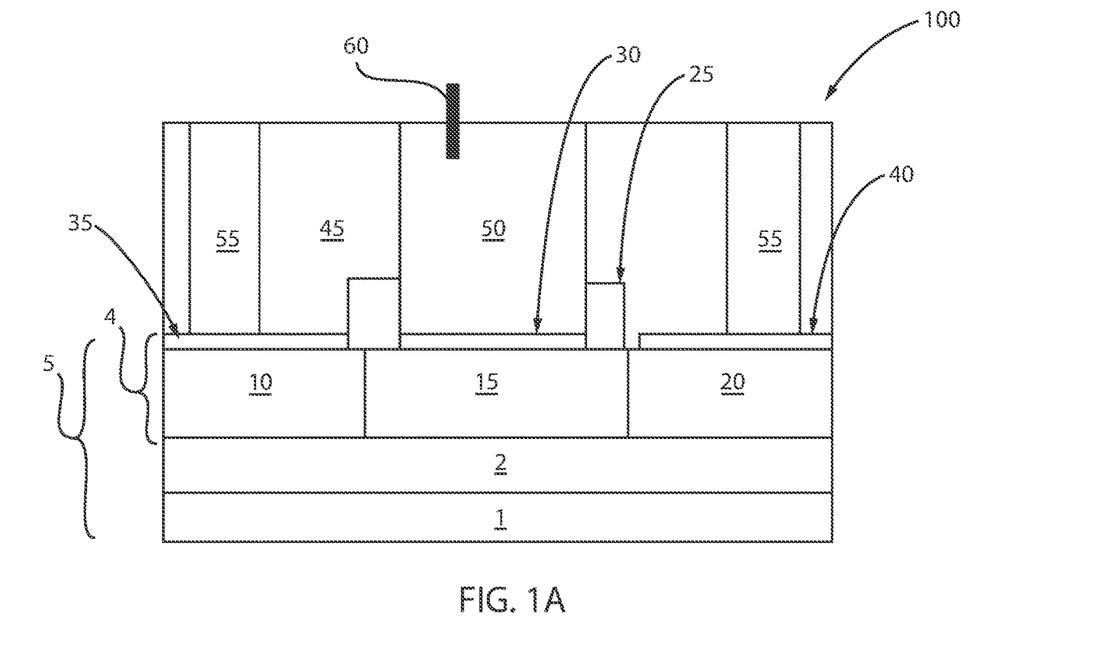
FIG. 1A is a side cross-sectional view of a bipolar junction transistor (BJT) including a metal containing contact from the base region of the BJT that extends into a reservoir for detecting biomolecules, in accordance with one embodiment of the present disclosure.

FIG. 1A depicts one embodiment of a bipolar junction transistor (BJT) 100 including a metal containing contact 30 from the base region 15 of the BJT 100 that extends into electrical communication with a reservoir 50 for detecting biomolecules within a liquid solution being contained within the reservoir 50. The BJT 100 typically includes an emitter region 10 and a collector region 20 on opposing sides of the base region 15. The emitter region 10 and the collector region 20 have an opposite conductivity type as the base region 15. The term "conductivity type" as used herein denotes whether a region has a p-type conductivity or an n-type conductivity. As used herein, "p-type" refers to the addition of impurities to a semiconductor that creates deficiencies of valence electrons. In a type IV semiconductor material, such as germanium or silicon, examples of p-type dopants include but are not limited to boron, aluminum, gallium and indium. As used herein, "n-type" refers to the addition of impurities that contributes free electrons to a semiconductor. In a semiconductor material composed of a type IV semiconductor, such as germanium or silicon, examples of n-type dopants, i.e., impurities, include but are not limited to, antimony, arsenic and phosphorous.

In the embodiment that is depicted in FIG. 1A, the emitter region 10, base region 15 and collector region 20 are formed in the semiconductor on insulator (SOI) layer 4 of a semiconductor on insulator (SOI) substrate 5. In some embodiments, the SOI layer 4 that provides the site for the emitter region 10, the base region 15 and the collector region 20 is composed of a silicon-containing material. Examples of silicon containing materials that are suitable for SOI layer 4 that contains the emitter region 10, the base region 15 and the collector region 20 include silicon (Si), silicon germanium (SiGe), silicon germanium doped with carbon (SiGe:C), silicon carbon (Si:C), and combinations thereof. In other embodiments, the SOI layer 4 may be principally composed of another type IV semiconductor, such as germanium (Ge).

In yet other embodiments, the SOI layer 4 may be composed of a compound semiconductors, such as III-V semiconductors. It is noted that the above list of semiconductor materials is provided for illustrative purposes only, and is not an exhaustive list, as other semiconductor materials may be suitable for the semiconductor material of the emitter region 10, base region 15, and the collector region 20 of the BJT 100. The semiconductor material that provides the emitter region 10, base region 15 and the collector region 20 may have a single crystal crystalline structure, multi-crystalline or poly-crystalline crystal structure. The dopant that dictates the conductivity type of the emitter region 10, base region 15 and the collector region 20 may have introduced via ion implantation or in situ doping. In situ doping is the doping of a semiconductor material as it is formed. The SOI substrate 5 may also include a buried oxide layer 2 and base semiconductor layer 1.

Referring to FIG. 1A, in some embodiments, an electrically conductive contact 30, 35, 40 may be formed to each of the emitter region 10, the base region 15 and the collector region 20. The electrically conductive contact 30 that is present in electrical communication with the base region 15 may provide the sensing surface of the bio-molecule sensor 100. As used herein, the term "electrical communication" means that a first structure or material can conduct electricity, i.e., is electrically conductive, to a second structure or material. The term "electrically conductive' as used herein denotes a material typically having a room temperature conductivity of greater than $10^7$ Siemens/m. In some embodiments, the material of the electrically conductive contact 30, 35, 40 is a metal containing material. Examples of electrically conductive metals that are suitable for the electrically conductive contacts 30, 35, 40 include silver (Ag), gold (Au), tungsten (W), nickel (Ni), titanium (Ti), molybdenum (Mo), tantalum (Ta), copper (Cu), platinum (Pt), ruthenium (Ru), iridium (Jr), rhodium (Rh), and rhenium (Re), and alloys that include at least one of the aforementioned conductive elemental metals. The electrically conductive contacts 30, 35, 40 may also be metal nitrides, such as titanium nitride (TiN), tantalum nitride (TaN), tungsten nitride (WN), and a combination thereof. In yet another embodiment, the electrically conductive contacts 30, 35, 40 may be composed of a metal semiconductor alloy. For example, the electrically conductive contacts 30, 35, 40 can be composed of a silicide, which is an alloy of silicon and a metal element. Examples of silicides that are suitable for the electrically conductive contacts 30, 35, 40 include nickel monosilicide, nickel disilicide, cobalt silicide, tungsten silicide and combinations thereof. It is noted that the above examples of compositions for the electrically conductive contacts 30, 35, 40 are provided for illustrative purposes only, and are not intended to limit the present disclosure. In some embodiments, the electrically conductive contact 30 to the base region 15 of the BJT should have a resistance of less than 1 ohm, as functionalized to provide the sensing surface for the BJT biomolecule.

The electrically conductive contacts 30, 35, 40 may be formed using deposition methods in combination with etch processes or block masks to select which regions of the SOI layer that the electrically conductive contacts 30, 35, 40 are formed on. For example, the electrically conductive contact 30 to the emitter region 10 is separated from each of the electrically conductive contacts 30, 40 to the base region 15 and the collector region 20, respectively. Further, the electrically conductive contact 40 to the collector region 20 is separated from the electrically conductive contacts 35, 30 to the emitter and base regions 10, 15, respectively. The electrically conductive contact 30 to the base region 15 is separated from the electrically conductive contacts 35, 40 to the emitter region 10 and the collector region 20. In some embodiments, to ensure electrical isolation between the electrically conductive contacts 35, 40 to the emitter and collector region 10, 20 and the electrically conductive contact 30 to the base region 15, a dielectric spacer 25 is formed on the interface between the emitter region 10 and the base region 15, as well as the interface between the base region 15 and the collector region 20. The dielectric spacer 25 is positioned to separate the electrically conductive contact 30 to the base region 15 from the electrically conductive contacts 35, 40 to the emitter and collector regions 10, 20. The dielectric spacer 25 may be composed of any dielectric material, such as an oxide, nitride or oxynitride material. For example, the dielectric spacer 25 may be composed of silicon oxide ($SiO_2$), silicon nitride ($Si_3N_4$) or silicon oxynitride.

Still referring to FIG. 1A, an interlevel dielectric 45 may be present on the upper surface of the SOI layer 4 including the electrically conductive contacts 30, 35, 40 and the dielectric spacer 25. Openings may be present through the interlevel dielectric to provide a reservoir 50 to for containing the liquid suspension to be measured by the sensing surface of the electrically conductive contact 30 to the base region 15. The electrically conductive contact 30 is the sensing surface connected to the base of the bipolar junction transistor (BJT). A voltage is applied to the solution using a reference electrode 60, and this applied voltage is referred as $V_{ref}$. Openings may also be provided to provide metal studs 55 to the electrically conductive contacts 35, 40 to the emitter region 10 and the collector region 20. The metal stud 55 to the electrically conductive contact 35 to the emitter region 10 is the structure through which the emitter voltage (Ve) is applied to the bipolar junction transistor (BJT). The metal stud 55 to the electrically conductive contact 40 to the collector region 20 is the structure through which the collector current (Ic) is measured.

It is noted that the embodiment depicted in FIG. 1A is only one embodiment of the present disclosure, and that it is not necessary that the reservoir 50 be embedded within an interlevel dielectric. The reservoir 50 may be provided by any vessel that can contain a liquid suspension, in which the sensing surface to the electrically conductive contact 30 to the base region 15 may be positioned. For example, the reservoir 50 may be a glass or plastic container. In some embodiments, the geometry of the reservoir 50 is selected so that the base of the reservoir 50 has an area ranging from 1 $\mu m^2$ to 1 $mm^2$. In other examples, the reservoir 50 is selected so that the base of the reservoir 50 has an area ranging from 1.25 $\mu m^2$ to 0.75 $mm^2$. It Is noted that the reservoir 50 can have any geometry and size, so long as the reservoir 50 can contain the sensing surface.

The electrically conductive contact 30 to the base region 15 of the BJT 100 provides the sensing surface of the bio-molecule sensor. The semiconductor device, e.g., BJT 100, measures the net charges within the liquid sample within a Debye length from the sensing surface, e.g., sensing metallic film. Typically, the Debye length decreases with increasing ion concentration in the solution with square root dependence. The Debye length can be important because the charges outside this length as measured from the sensing surface cannot be electrically detected. For example, when the electrically conductive contact 30 to the base region 15 is composed of silver chloride (AgCl), the BJT bio-molecule sensor 100 may be employed to detect the presence of Chlorine ($Cl^-$) ions in a liquid solution. The silver chloride (AgCl) of the sensing surface may be the base material of the electrically conductive contact 30, or may be a coating to functionalize the electrically conductive contact 30 for detecting the presence of chlorine (Cl−) ions in a liquid solution. In another embodiment, the electrically conductive contact 30 to the base region 15 is composed of titanium nitride (TiN), wherein the titanium nitride (TiN) sensing surface can detect the pH of a liquid solution, the pH of the liquid solution then being correlated to the concentration of protons ($H^+$) in the liquid solution. In yet another embodiment, the surface of the electrically conductive contact 30 to the base region 15 is chemically modified with proteins and/or ions for binding with proteins and/or ions in the liquid solution. For example, to detect strepavidin protein, the sensing surface can be coated with biotin, because biotin specifically binds the streptavidin protein.

In each of the above examples, during measurement of the liquid suspension by the BJT biomolecule sensor, charged bio molecules, e.g., chlorine ($Cl^-$) and protons ($H^+$), adhere to the sensing surface of the electrically conductive contact 30 to the base region 15, which changes the electrically properties of the biomolecule sensor, such as the collector current (Ic).

Figure 1B:
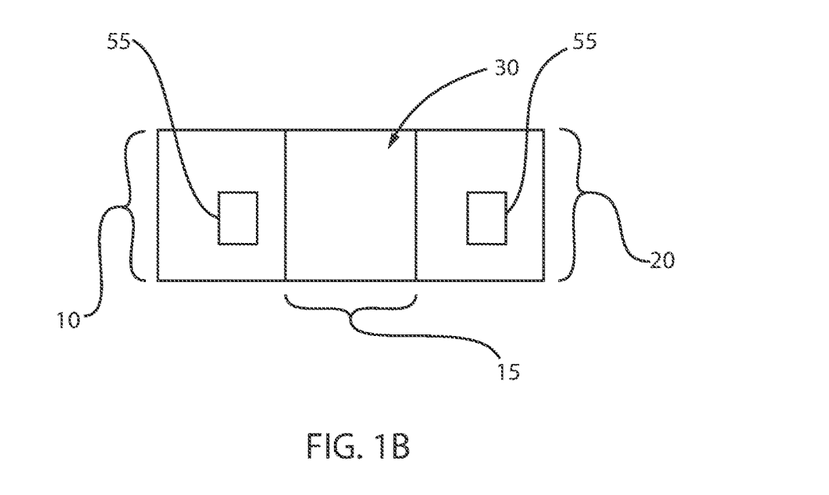
FIG. 1B is a top down view depicting a base contact that provides the sensing surface for the BJT molecular sensor that is present within the perimeter of the base region, in accordance with one embodiment of the present disclosure.
Figure 1C:
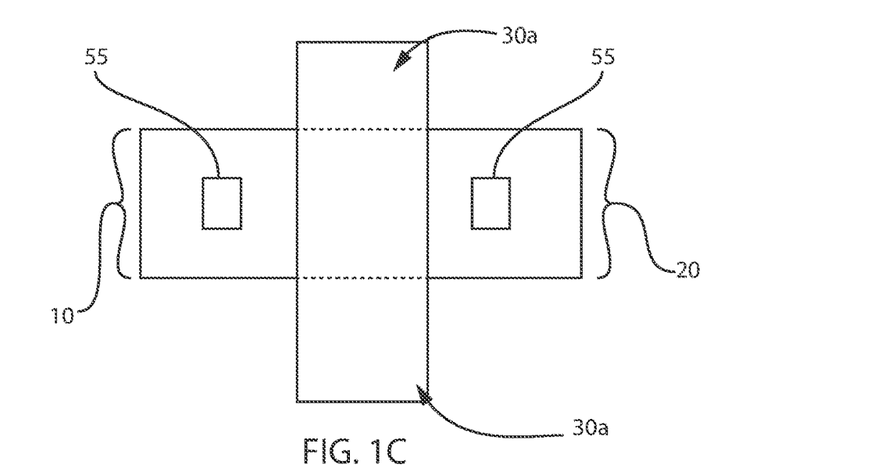
FIG. 1C is a top down view depicting a base contact that provides the sensing surface for the BJT molecular sensor that extends outside the perimeter of the base region, in accordance with one embodiment of the present disclosure.

In some embodiments, only the sensing surface of the electrically conductive contact 30 to the base region is in contact with, e.g., immersed in, the liquid solution that is contained within the reservoir 50 from which the measurements are taken. In some embodiments, to provide that only the sensing surface of the electrically conductive contact 30 to the base region 15 is in contact with the liquid solution, the reservoir 50 is formed directly atop the sensing surface, the electrically conductive contact 30 and the base region 15, as depicted in FIG. 1B. FIG. 1B depicts an embodiment of the present disclosure in which an entirety of the electrically conductive contact 30 provides the sensing surface of the BJT biomolecule sensor 100. In the embodiment depicted in FIG. 1B, the reservoir 50, the electrically conductive contact 30, and the sensing surface are directly atop and aligned with the perimeter of the base region 15. In other embodiments, the electrically conductive contact includes an extension portion 30a. The extension portion 30a is the portion of the electrically conductive contact 30 that is not present overlying (within the perimeter) of the base region 15. FIG. 1C depicts one embodiment of an electrically conductive contact 30 having an extension portion 30a. In some embodiments, the extension portion 30a of the electrically conductive contact 30 is treated to provide the sensing surface, wherein the sensing surface, i.e., extension portion 30a, of the electrically conductive contact 30 is the only portion of the electrically conductive contact 30 that is present immersed within the liquid suspension, as depicted in FIGS. 2 and 3.

As depicted in FIGS. 1A, 1B, 1C and 2, the BJT biomolecule sensor 100 may have a lateral orientation. By having a "lateral orientation" it is meant that the emitter region 10, base region 15 and collector region 20 are present on a substrate and are orientated left to right, or right to left, as depicted in FIGS. 1A, 1B, 1C and 2. The BJT biomolecule sensor 100 may also include a vertical orientation. By "vertical orientation" it is meant that the emitter region 10, base region 15 and collector region 20 are orientated in a stacked arrangement, e.g., from top to bottom, on a surface of a substrate, as depicted in FIG. 3.

Figure 2:
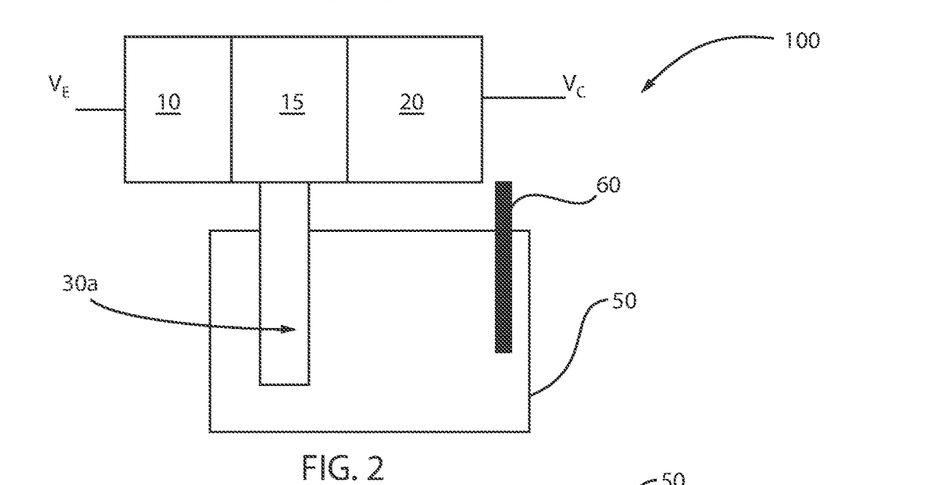
FIG. 2 is a side cross-sectional view of a BJT molecular sensor having a lateral orientation, in accordance with one embodiment of the present disclosure.

FIG. 2 depicts one embodiment of a lateral orientation BJT biomolecule sensor 100 having an extension portion 30a that provides the sensing surface of the electrically conductive contact 30 to the base region 15 that is immersed within the liquid solution housed by the reservoir 50. As depicted in FIG. 2, in some embodiments, the sensing surface portion, i.e., extension portion 30a, of the electrically conductive contact 30 is the only portion of the electrically conductive contact 30 that is immersed within the liquid solution. In this example, the reservoir 50 is remotely positioned from the base region 15 of the BJT molecule sensor 100. Although the sensing surface is depicted as being an extension of the electrically conductive contact 30 to the base region 15, embodiments have been contemplated in which the sensing surface is physically separated from the electrically conductive contact 30 to the base region 15 but in electrical communication to the electrically conductive contact 30 to the base region 15 through an electrically conductive wire. A reference electrode 60 is also present immersed in the liquid suspension being contained by the reservoir 50.

Figure 3:
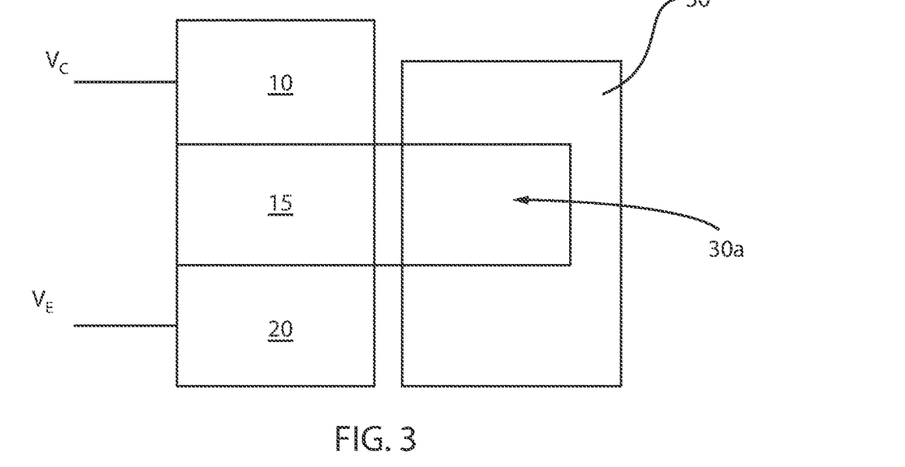
FIG. 3 is a side cross-sectional view of a BJT molecular sensor having a vertical orientation, in accordance with one embodiment of the present disclosure.

FIG. 3 depicts one embodiment of a vertical orientation BJT biomolecule sensor 100. Similar to the lateral orientation BJT biomolecule sensor that is depicted in FIG. 2, the sensing surface portion, i.e., extension portion 30a, of the electrically conductive contact 30 to the base region 15 of the vertically orientation BJT biomolecule sensor 100 is the only portion of the electrically conductive contact 30 that is immersed within the liquid solution. Also similar to the lateral orientation BJT biomolecule sensor, embodiments of the vertical orientation BJT sensor may include a sensing surface that is physically separated from the electrically conductive contact 30 to the base region 15, but in electrical communication to the electrically conductive contact 30 to the base region 15 through an electrically conductive wire. A reference electrode 60 may also be present immersed in the liquid suspension being contained by the reservoir 50.

Figure 4A:
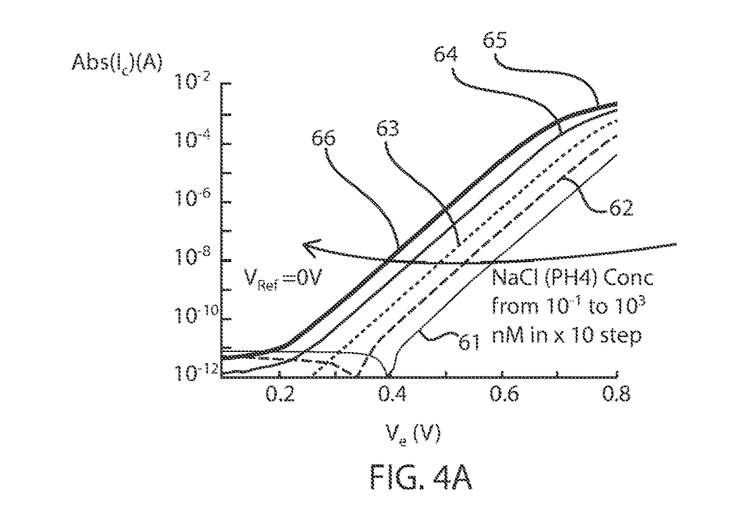
FIG. 4A is a plot of collector current curves measured in aqueous solution with different NaCl concentration using a PNP BJT sensor with silver chloride (AgCl) as the sensing surface, in accordance with one embodiment of the present disclosure.
Figure 4B:
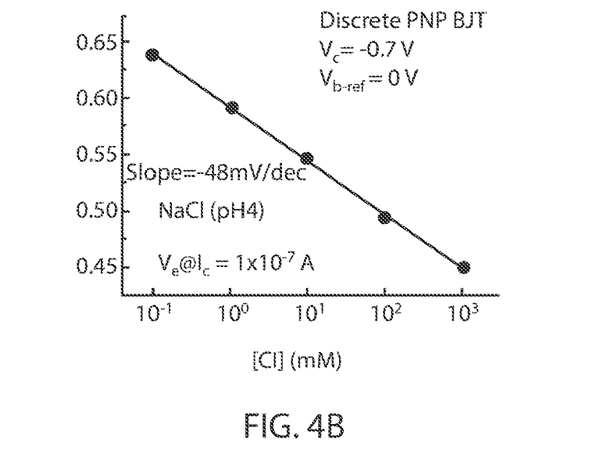
FIG. 4B is a plot obtained from the data shown in FIG. 4A for PNP sensor. In plot FIG. 4B, the y-axis is the emitter voltage ($V_e$) value at which the collector current ($I_c$)=$10^{-7}$ A corresponding to different NaCl concentrations of the solution. The plot shows the dependence of the sensing signal as a function of $Cl^-$ concentration of the solution.
Figure 4C:
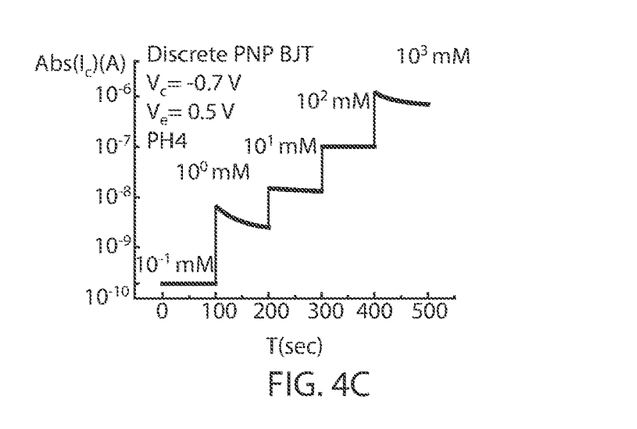
FIG. 4C shows the dependence of the sensing current $I_c$ measured at a fixed emitter voltage ($V_e$)=0.5V as a function of $Cl^-$ concentration in the solution using PNP BJT sensor.

FIGS. 4A-4C illustrate the electrical performance of a PNP BJT molecular sensor for measuring a concentration of chloride (Cl-) ions within a liquid solution using a sensing surface that is composed of silver chloride (AgCl). FIG. 4A is a plot of collector current (Abs (Ic) (A)) as a function of a difference of voltage (($V_e$-$V_{ref}$)(V)) between the voltage that is applied to the emitter ($V_e$) and the reference voltage ($V_{ref}$). The reference voltage ($V_{ref}$) is the voltage applied to the reference electrode 60 that is depicted in FIGS. 2 and 3. The liquid solution being measured in FIG. 4A is composed of sodium chloride (NaCl). The plot identified by reference number 61 is a 0.1 mM concentration of sodium chloride (NaCl) in a pH buffer of 4. The plot identified by reference number 62 is a 1 mM concentration of sodium chloride (NaCl) in water. The plot identified by reference number 63 is a 10 mM concentration of sodium chloride (NaCl) in a pH buffer of 4. The plot identified by reference number 64 is a 100 mM concentration of sodium chloride (NaCl) in a pH buffer of 4. The plot identified by reference number 65 is a 1000 mM concentration of sodium chloride (NaCl) in a pH buffer of 4. As illustrated by the plots included in FIG. 4A, as the concentration of sodium chloride (NaCl) is increased, the voltage needed to achieve a given collector current of the PNP BJT molecular sensor decreases. Specifically, a shift in the collector current curves of approximately 48 mV/decade was measured, as plotted in FIG. 4B. In the plot depicted in FIG. 4B, the collector voltage (Vc) was equal to −0.7 V and the reference voltage (Vref) was equal to 0 V. The shift is to the left as indicated by the arrow 66 in FIG. 4A with increasing chloride ($Cl^-$) concentration. FIG. 4C illustrates the dependence of the sensing current (Ic) measured at a fixed emitter voltage (Ve), e.g., 0.5V, on the chloride ion concentration in the solution for a PNP BJT molecular sensor.

The subthreshold swing (SS), i.e., the slope of the semi-log plot of current versus voltage, is approximately 60 mV/decade at room temperature, which is smaller than the subthreshold swing of field effect transistors (FETs), which provide another type of biomolecule sensor that is less sensitive than the BJT biomolecule sensors that are disclosed herein.

Figure 5A:
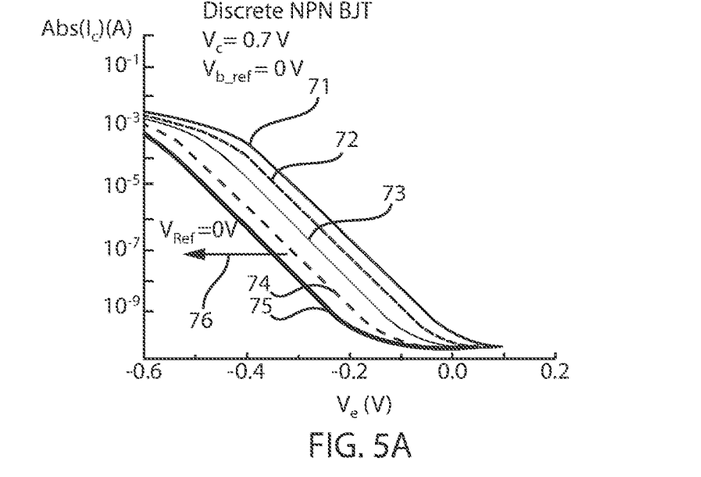
FIG. 5A is a plot of current curves measured from an NPN BJT molecular sensor with silver chloride (AgCl) as the sensing surface. The collector current ($I_C$) is measured as function of applied emitter voltage ($V_e$) for different NaCl concentrations of the solution, in accordance with one embodiment of the present disclosure.
Figure 5B:
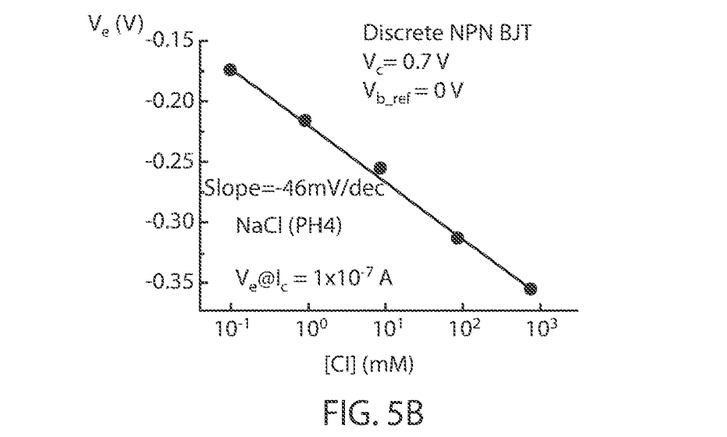
FIG. 5B is a plot obtained from the data shown in FIG. 5A for NPN BJT molecular sensor. In plot FIG. 5B, the y-axis is the emitter voltage ($V_e$) value at which the collector current ($I_c$)=$10^{-7}$ A corresponding to different NaCl concentrations of the solution. The plot shows the dependence of the sensing signal as a function of $Cl^-$ concentration of the solution.
Figure 5C:
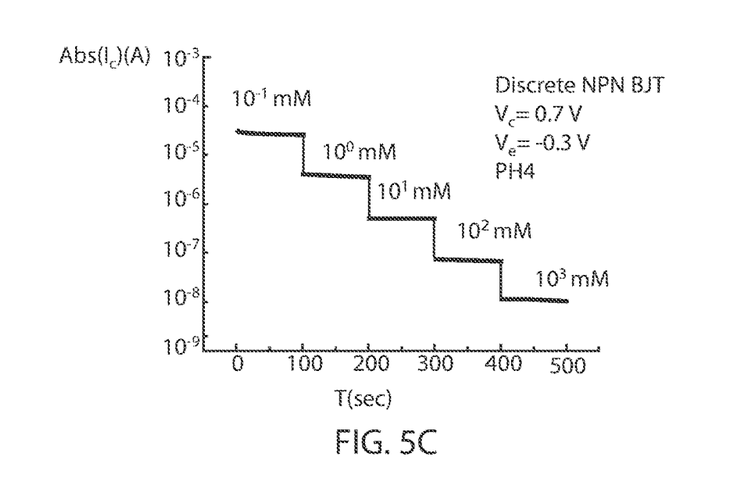
FIG. 5C shows the dependence of the sensing current ($I_c$) measured at a fixed emitter voltage $V_e$=−0.3V as a function of $Cl^-$ concentration in the solution using NPN BJT molecular sensor.

FIGS. 5A-5C illustrate the electrical performance of a NPN BJT molecular sensor for measuring a concentration of chloride (Cl⁻) ions within a liquid solution using a sensing surface that is composed of silver chloride (AgCl). The NPN BJT molecular sensor illustrates that an NPN BJT molecular sensor will display electrical performance having a substantially inverse relationship to the PNP BJT molecular sensor that provided the data plotted in FIGS. 4A-4C. The liquid solution that provided that data depicted in FIGS. 4A-4C is similar to the liquid solution that provides the data in FIGS. 5A-5C. The plot identified by reference number 71 is a 0.1 mM concentration of sodium chloride (NaCl) in a pH buffer of 4. The plot identified by reference number 72 is a 1 mM concentration of sodium chloride (NaCl) in water. The plot identified by reference number 73 is a 10 mM concentration of sodium chloride (NaCl) in a pH buffer of 4. The plot identified by reference number 74 is a 100 mM concentration of sodium chloride (NaCl) in a pH buffer of 4. The plot identified by reference number 75 is a 1000 mM concentration of sodium chloride (NaCl) in a pH buffer of 4. As illustrated by the plots included in FIG. 5A, as the concentration of sodium chloride (NaCl) is increased, the voltage needed to achieve a given collector current of the NPN BJT shifts to the left. Specifically, a shift in the collector current curves of approximately −46 mV/decade was measured, as plotted in FIG. 5B. In the plot depicted in FIG. 5B, the collector voltage (Vc) was equal to −0.7 V and the reference voltage (Vref) was equal to 0 V. The shift is to the left as indicated by the arrow 76 in FIG. 5A with increasing chloride (Cl⁻) concentration. FIG. 5C illustrates that dependence of the sensing current (Ic) measured at a fixed emitter voltage (Ve)=−0.3V on the chloride ion concentration in the solution for an NPN BJT sensor.

Figure 6:
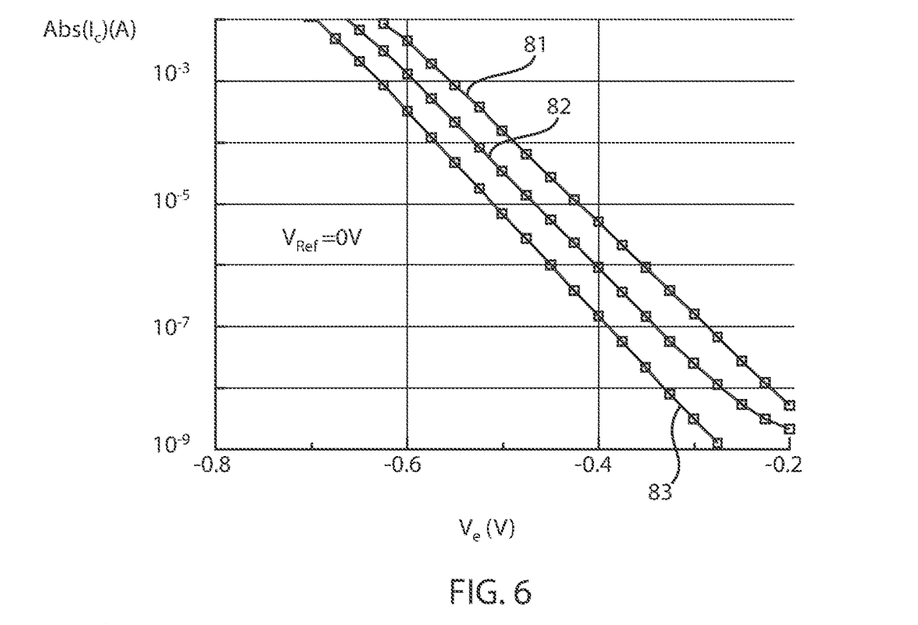
FIG. 6 is a plot depicting temperatures inferred from a NPN BJT sensor. The collector current ($I_C$) is measured as a function of emitter voltage ($V_e$) at three different temperatures. At each temperature, the current is observed to have an exponential dependence on the emitter voltage (Ve) with an exponent=1/kT, where k is Boltzmann constant and T is the temperature in Kelvin. Hence, the measured exponent value provides measure of the temperature.

In some embodiments, the NPN and PNP BJT molecular sensors that employ a sensing surface that is composed of titanium nitride (TiN) can also measure the temperature of the liquid solution. More specifically, the temperature can be correlated to changes in the slope of a semi-log plot of current versus using the current taken from the collector region 20 of the BJT molecular sensor. FIG. 6 depicts a semi-log plot of current versus voltage curves taken from an NPN BJT biomolecule sensor in which the Y-axis is a current measured from the collector region (Abs (Ic)(A)) and the X-axis is a measurement of a difference of voltage ((V$_e$−V$_{ref}$)(V)) between the voltage that is applied to the emitter (V$_e$) and the reference voltage (V$_{ref}$) applied to the solution. In the example that is depicted in FIG. 6, the collector current (Ic) curves are measured at three different temperatures. The plot of the collector current (Ic) identified by reference number 81 was taken from a liquid solution having a temperature of about 65° C. The slope of the plot identified by reference number 81 was approximately 66.4 mV/decade. The plot of the collector current (Ic) identified by reference number 82 was taken from a liquid solution having a temperature of about 45° C. The slope of the plot identified by reference number 81 was approximately 62.7 mV/decade. The plot of the collector current (Ic) identified by reference number 83 was taken from a liquid solution having a temperature of about 25° C. The slope of the plot identified by reference number 81 was approximately 59.7 mV/decade. As indicated by the plots including in FIG. 6, the slope of the collector current curves becomes shallower with increasing temperature. The following equation was used to extract the temperature from the data recorded in FIG. 6:

$$Ic = Io * \exp((Vref - Ve)/kT) \quad \text{Equation 1:}$$

wherein Io is a constant independent of applied emitter (Ve) and reference (Vref) voltages (ref: "Physics of Bipolar Devices" by SM Sze, (John Wiley & Sons)), T is the temperature and k is a Boltzmann constant. In view of Equation 1, when the collector current is plotted in a log scale, there is an inverse relationship between the slope of the collector current (Ic) measured from the BJT measuring the concentration of the liquid suspension that is in electrical communication to the base region 15 of the BJT through a sensing surface composed of TiN and the temperature of the liquid. This relationship between collector current and temperature is the same for both NPN and PNP BJTs. Therefore, in some embodiments, the NPN and PNP BJT biomolecule sensors can provide simultaneous measurement of biomolecule concentration within a liquid suspension and a measurement of the temperature of the liquid suspension.

It is noted that the above example of NPN and PNP BJT biomolecule sensors including a sensing surface composed of silver chloride (AgCl) is provided for illustrative purposes only, and is not intended to limit the present disclosure. For example, other materials that may simultaneously provide for measurements of biomolecule concentration and temperature may include Au, Ag, TiN, TaN, AgCl, biotin coated gold, aptamer coated gold and antibody protein coated gold or titanium nitride.

In another example, the sensing surface of the electrically conductive contact 30 to the base region 15 of the BJT biomolecule sensor may be composed of titanium nitride (TiN), wherein the titanium nitride sensing surface measures the pH of the liquid suspension that is contained within the reservoir is correlated to a concentration of protons (H+) through the following equation:

$$pH = -\log 10[H+] \quad \text{Equation 2:}$$

The temperature of the liquid suspension may also be measured using a titanium nitride (TiN) sensing surface.

In another example, when the sensing surface of the BJT is functionalized with biotin ($C_{10}H_{16}N_2O_3S$) in order to detect streptavidin protein and the BJT is an NPN transistor, the collector current (Ic), i.e., Ic can increase or decrease depending on the pH of the solution, with increasing concentration of strepavidin protein within the liquid solution being contained in the reservoir 50. In another example, when the sensing surface of the BJT is functionalized with biotin ($C_{10}H_{16}N_2O_3S$) in order to detect streptavidin protein and the BJT is an PNP transistor, the collector current (Ic) changes, i.e., Ic can increase or decrease depending on the pH of the solution, with increasing concentration of strepavidin protein within the liquid solution being contained in the reservoir 50.

In some embodiments, the BJT biomolecule sensor can be used in a method of measuring concentration of ions in a solution that includes providing a solution of ions, and providing electrical communication between a base region 15 of a bipolar junction transistor through an extension of a metal containing contact from the base to the solution of ions, the portion of the metal containing contact immersed in the solution of ions being a sensing surface; and measuring current from a collector region 20 of the bipolar junction transistor, wherein changes in current being measured from the collector region 20 denotes changes in concentration of ions in the solution of ions. In some embodiments, to measure the current from the collector region 20, voltage (Ve) is applied to the emitter region 10 through the metal stud 55 to the electrically conductive contact 35 to the emitter region 10. The voltage ($V_{ref}$) is applied to the solution using a reference electrode immersed in the solution. The voltage (Ve) that is applied to the emitter region 10 typically ranges from −2 Volts to 2 Volts. In some embodiments, the voltage (Ve) that is applied to the emitter region 10 may range from 0 Volts to 1 Volts for PNP BJT sensors and 0 to −1 V for NPN BJT sensors. During the measurement of the collector current (Ic), a reference electrode 60 is also present in the reservoir 50 that is containing the liquid solution being measured. The voltage ($V_{ref}$) applied to the reference electrode 60 is some examples may be 0 volts, but other voltages for the reference voltage have been considered.

In another aspect, a combined semiconductor device and surface plasmon resonance spectroscopy (SPR) based biosensor is provided. Since two disparate sensing methods (optical/electrical) are simultaneously sensing the same molecules, the probability for detecting of a false positive is reduced. The semiconductor device may be a BJT, as described with reference to FIGS. 1-6, or may be a field effect transistor (FET). The semiconductor device may detect change in the charge density near the sensing surface, which can be correlated to a concentration of biomolecules. SPR is an optical sensing method which detects molecules by measuring change in the refractive index at the interface of the reflecting surface, such as gold. Surface plasmon resonance (SPR) is the collective oscillation of electrons in a solid stimulated by incident light. The resonance condition is established when the frequency of light photons matches the natural frequency of surface electrons oscillating against the restoring force of positive nuclei. SPR may be used to determine refractive index of a coating, coating thickness, surface density of adsorbed species etc. from a concentration of biomolecules from a testing sample.

Referring to FIGS. 7A-8B, in some embodiments, the SPR detector typically includes a light source 85, a reflective surface 90 that will support a surface plasmon, a spectrometer 95 (usually a CCD detector), and a polarizer 105. In the embodiments depicted in FIGS. 7A and 7B, the liquid suspension 111 from which the biomolecule measurements are made are in contact with a sensing surface 112 of opposite the surface of the reflective surface 90 that the light from the light source 85 is incident. In the embodiments depicted in FIGS. 7A and 7B, the light from the light source 85 travels through a prism 110 and glass surface 113, as well as traveling through the liquid suspension 111, into contact with the reflective surface 90. The incident light does not actually pass through the solution before contacting the reflecting surface. The evanescent wave from the light extends some distance into the analyte solution. Following contact with the reflective surface 90, the reflected light travels through the polarizer 105 into the detector 95. In the embodiments depicted in FIGS. 8A and 8B, the light from the light source 85 travels through a glass surface 113 and the liquid suspension 111 from which the bianalyte contacts a grated reflective surface 90. Following contact with the grated reflective surface 90, the reflected light travels through the polarizer 105 into the spectrometer 95. The light source 85 can be a broad band source, but is typically a laser. For example, the light source 85 may be composed of light at different wavelengths, e.g., from 360 nm to 2000 nm. The spectrometer 95 (spectrophotometer, spectrograph or spectroscope) is an instrument used to measure properties of light over a specific portion of the electromagnetic spectrum.

Figure 7A:
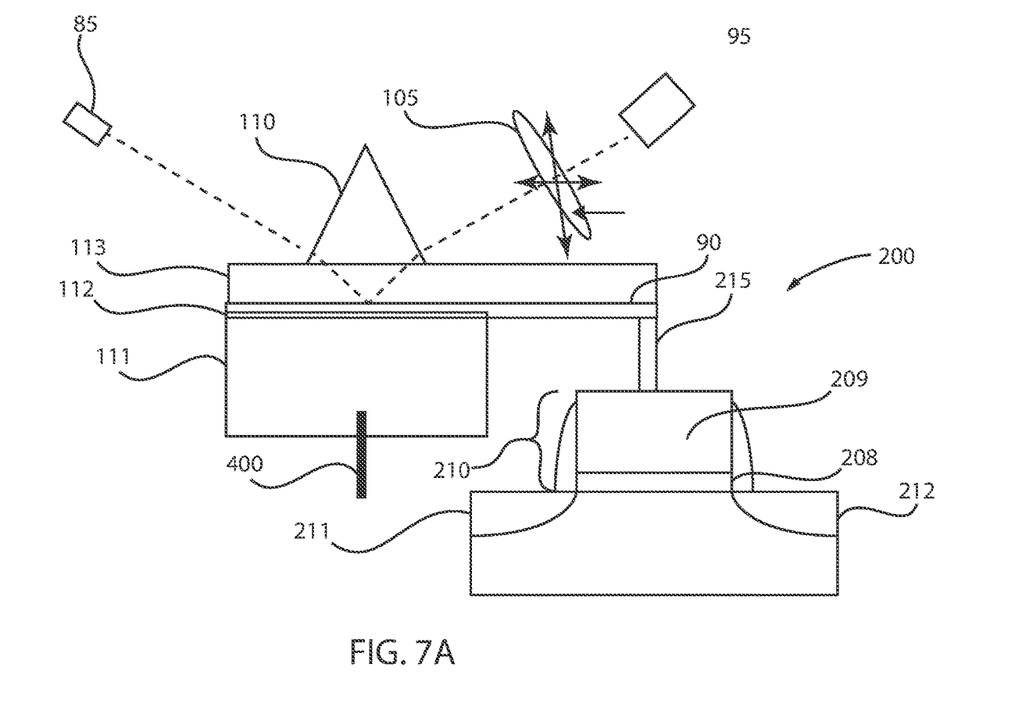
FIG. 7A is a side cross-sectional view depicting a combined surface plasmon resonance (SPR) and extended gate structure field effect transistor (FET) biomolecule sensor including a smooth metal containing sensing surface, in accordance with one embodiment of the present disclosure.
Figure 7B:
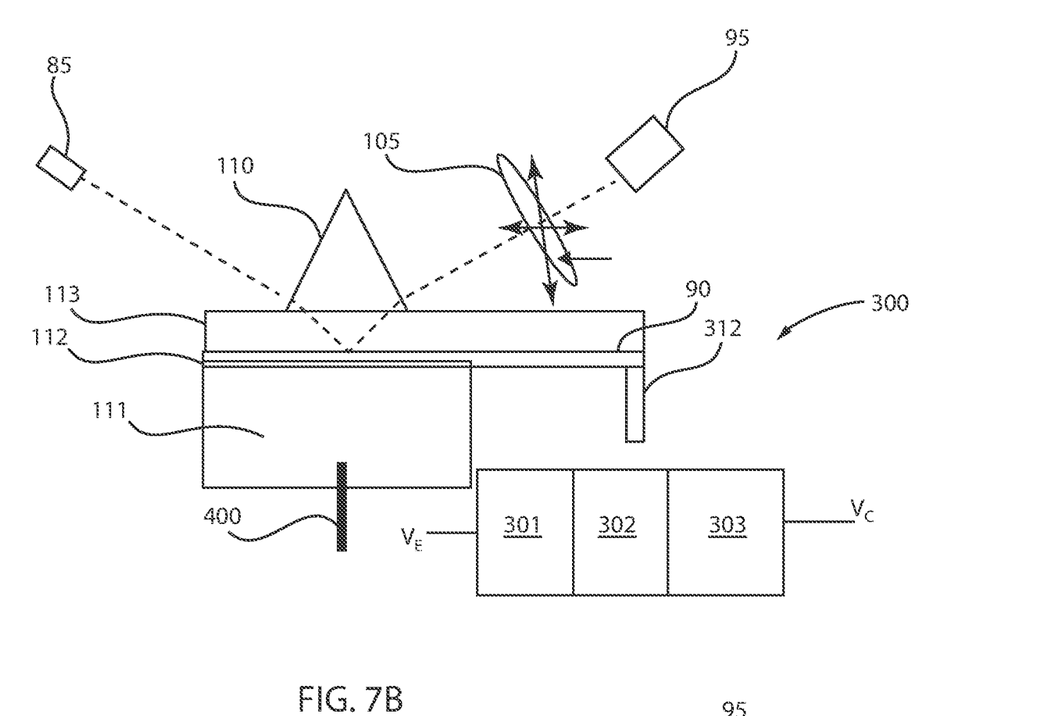
FIG. 7B is a side cross-sectional view depicting a combined surface plasmon resonance (SPR) and bipolar junction transistor (BJT) having an extended base contact biomolecule sensor including a smooth metal containing sensing surface, in accordance with one embodiment of the present disclosure.

SPR sensors are thin film refractometers that measure changes in the refractive index occurring at the metal surface, i.e., reflective surface 90, supporting a surface plasmon. A surface plasmon excited by light wave propagates along the metal film, i.e., reflective surface 90, and its evanescent field probes the medium, i.e., liquid containing sample 111, that is in contact with the reflective surface 90. A change in the reflective index of the dielectric at or near the interface gives rise to a change in the propagation constant of the surface plasmon, which through a coupling condition alters the characteristics of the light wave coupled to the surface plasmon (e.g., coupling angle, coupling wavelength, intensity phase). For this reason, the light wave is modulated by the surface plasmon is measured, SPR sensors are classified as sensors with angular, wavelength, intensity or phase modulation, each of which are suitable for use with the SPR sensor disclosed herein. In the embodiments that are depicted in FIGS. 7A and 7B, a prism coupler 110 is employed to couple light to a plasmon surface. Embodiments employing the prism coupler 110 may employ any type of modulation described above. In the embodiments depicted in FIGS. 8A and 8B, a light excites plasmons via a grating coupler provided by a grated reflective surface 90.

In some embodiments, SPR affinity biosensors are sensing devices which include a biorecognition element that recognizes and is able to interact with a selected analyte causing a shift in the reflectance minimum, thereby translating the binding event into an output signal. The biorecognition elements are immobilized in the proximity of the surface of a metal film, i.e., reflective surface 90, supporting a surface plasmon. Analyte molecules in a liquid sample 111 in contact with the SPR sensor bind to the biorecognition elements, producing an increase in the refractive index at the sensor surface which is optically measured. The change in refractive index produced by the capture of biomolecules depends on the concentration of analyte molecules at the sensor surface, i.e., reflective surface 90, and the properties of the molecules. In some embodiments, if the binding occurs within a thin layer at the sensor surface of thickness h, the sensor response is proportional to the binding-induced refractive index charge which can be expressed as:

$$\Delta n = (dn/dc)(\Gamma/h) \qquad \text{Equation 3:}$$

wherein (dn/dc) denotes refractive index increment of the analyte molecules and F denotes the surface concentration in mass/area.

Figure 8A:
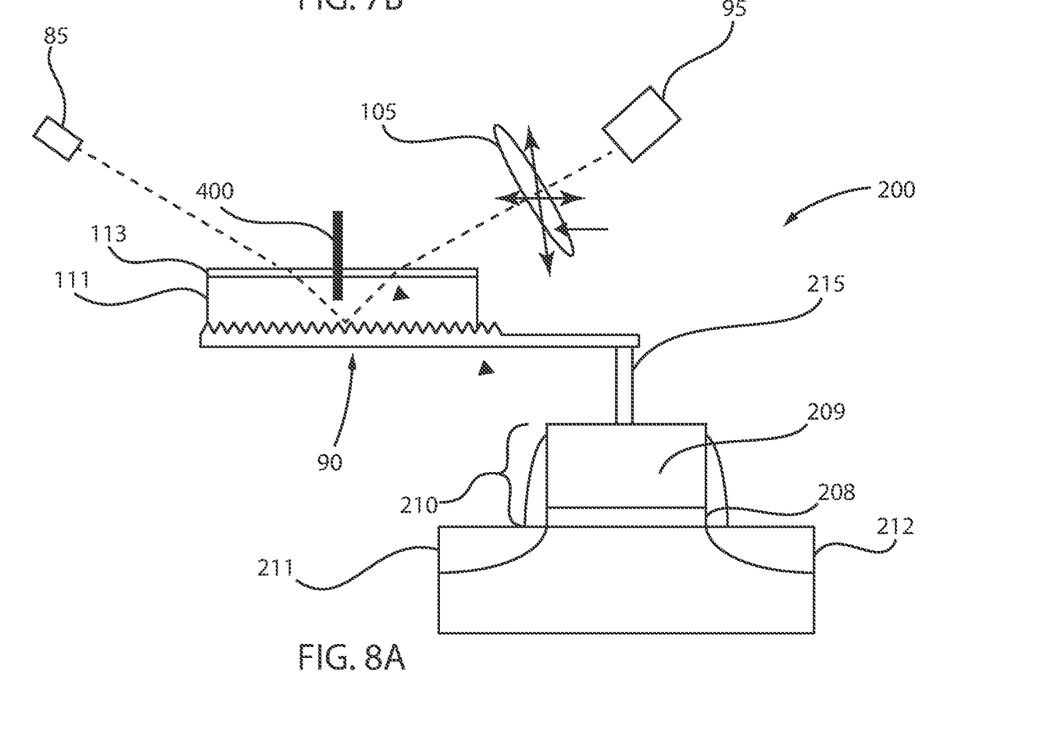
FIG. 8A is a side cross-sectional view depicting a combined surface plasmon resonance (SPR) and extended gate structure field effect transistor (FET) biomolecule sensor including a grated metal containing sensing surface, in accordance with one embodiment of the present disclosure.

To provide for a combined biomolecule sensor, the reflective surface 90 for the SPR provides the sensing surface for the semiconductor device as well, which provides a second biomolecule sensor. In the example that is depicted in FIGS. 7A and 8A, the semiconductor device is a field effect transistor (FET) 200. A field effect transistor (FET) 200 is a semiconductor device in which output current, i.e., source-drain current, is controlled by the voltage applied to a gate structure 210 to the semiconductor device. A field effect transistor has three terminals, i.e., gate structure 210, source region 211 and drain region 212. A "gate structure" means a structure used to control output current (i.e., flow of carriers in the channel) of a semiconducting device through electrical or magnetic fields. The gate structure 210 typically includes at least one gate dielectric 208 on the channel region of the device, and at least one gate conductor 209 on the at least one gate dielectric 208. As used herein, the term "channel" is the region underlying the gate structure 210 and between the source region 211 and drain region 212 of a semiconductor device that becomes conductive when the semiconductor device is turned on. As used herein, the term "drain" means a doped region in semiconductor device located at the end of the channel, in which carriers are flowing out of the transistor through the drain. As used herein, the term "source" is a doped region in the semiconductor device, in which majority carriers are flowing into the channel. As indicated above, the gate structure 200 of the FET is attached to the reflective surface 90 for the SPR, which provides the sensing surface 112 of the FET sensor. In some embodiments, the semiconductor device, e.g., FET sensor, measures the net charges of ions/molecules within the liquid sample within a Debye length from the sensing surface, e.g., sensing metallic film. In some examples, the sensing surface of the FET sensor may be a gold (Au) containing film, such as a gold (Au) film. In other embodiments, the reflective surface 90 for the SPR, which provides the sensing surface for the FET, may be composed of silver (Ag), such as a silver (Ag) metal film or a silver chloride (AgCl) film. Silver chloride (AgCl) alone typically does not support a surface plasmon wave, but silver chloride (AgCl) mixed with silver (Ag) nanoparticles will. The matter supporting the surface plasmon wave is a free electron species, such as various conducting metals. The metal could have a coating but it must be thin since it needs to be penetrated by the evanescent wave to interrogate the solution interface.

In some embodiments, in which the semiconductor device was a field effect transistor, the gate structure 210 is in electrical communication to the reflective surface 90 of the SPR through an extended portion 215 of the gate conductor 209 for the gate structure 210, as depicted in FIGS. 7A and 8A. The gate structure 210 including the extended gate portion 215 may be referred to as a FET having an extended gate. In another embodiment, in which the semiconductor device a FET, the FET is in electrical communication to the reflective surface 90 of SPR through wire bonding between the gate structure 210 and the reflective surface 90.

As the sensing surface 112 for the FET, the reflective surface 90 of the SPR may be composed of silver chloride (AgCl) so that the FET biomolecule sensor may be employed to detect the presence of Chlorine (Cl$^-$) ions in a liquid solution. The silver chloride (AgCl) of the sensing surface for the FET, i.e., reflective surface 90 of the SPR, may be a base material, or may be a coating to functionalize the reflective surface 90 for detecting the presence of chlorine (Cl–) ions in a liquid solution. In another embodiment, the reflective surface 90 of the SPR may be composed of titanium nitride (TiN), so that the sensing surface 112 for the FET biomolecule sensor can detect the pH of a liquid solution, the pH of the liquid solution then being correlated to the concentration of protons (H$^+$) in the liquid solution. In yet another embodiment, the surface of the reflective surface 90 of the SPR is chemically modified with proteins and/or ions for binding with proteins and/or ions in the liquid solution in order to function as the sensing element 112 of the FET biomolecule sensor. For example, to detect strepavidin protein, the sensing surface 112 can be coated with biotin, because biotin specifically binds the streptavidin protein.

In each of the above examples, during measurement of the liquid suspension 111 by the FET biomolecule sensor, charged bio molecules, e.g., chlorine (Cl$^-$) and protons (H$^+$), approach/adhere to the sensing surface 112 of the FET biomolecule sensor, i.e., the reflective surface 90 of the SPR, which changes the electrically properties of the biomolecule sensor, such as the collector current (Ic).

Figure 8B:
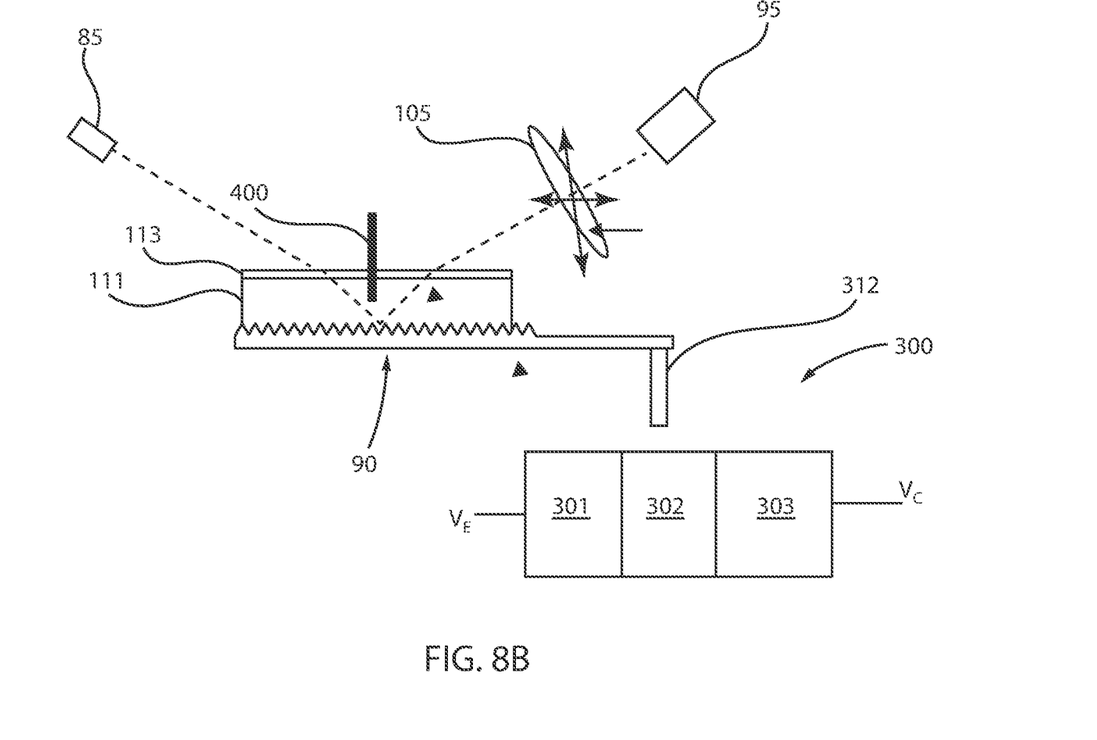
FIG. 8B is a side cross-sectional view depicting a combined surface plasmon resonance (SPR) and bipolar junction transistor (BJT) having an extended base contact biomolecule sensor including a grated metal containing sensing surface, in accordance with one embodiment of the present disclosure.

FIGS. 7B and 8B depict another embodiment of the present disclosure in which the semiconductor device that is in electrical communication with the reflective surface 90 of the SPR is a bipolar junction transistor (BJT) 300. The bipolar junction transistor (BJT) 300 that are depicted in FIGS. 7B and 8B includes an emitter region 301, base region 302 and collector region 303. The bipolar junction transistor 300 that are depicted in FIGS. 7B and 8B is similar to the biomolecule sensor provided by the bipolar junction transistor (BJT) 100 that is described above with reference to FIGS. 1-6. Therefore, the above description of the BJT 100 that is depicted in FIGS. 1-3 is suitable for the BJT 300 that is depicted in FIGS. 7B and 8B. For example, the description of the emitter region 10, the base region 15, and the collector region 20 that are depicted in FIGS. 1 and 2, is suitable for the emitter region 301, base region 302 and collector region 303 of the BJT 300 that is depicted in FIGS. 7B and 8B. Further, the above description of the electrically conductive contact 30 to the base region 15 for the BJT 100 described above with reference to FIGS. 1-6 is suitable for describing the sensing surface of the BJT 300 that is depicted in FIGS. 7B and 8B, in which sensing surface for the BJT 300 also provides the reflector surface 90 of the SPR. Similar to the embodiments in which the semiconductor device is a FET, the sensing surface of the BJT may be an extended portion 312 of the contact to the base region 302 of the BJT 300, or the sensing surface for the BJT may be connected to the base region 302 of the BJT 300 using a wired connection.

The sensors depicted in FIGS. 7A-8B, which combine SPR & FET sensing methods, provides optical measurements of refractive index and mass of the sample, as provided by the SPR sensor, and electrical measurements of electrical charge of the sample, as provided by the semiconductor device, e.g., FET and/or BJT.

To provide the combined functions of a reflector surface 90 for the SPR detector and a sensing surface for the semiconductor device, the reflector surface 90 may be a metal film having a thickness that is less than 150 nm. In some embodiments, the thickness of the metal film for the reflector surface 90 of the SPR detector and the sensing surface for the semiconductor device may range from 50 nm to 150 nm. In other embodiments, the thickness of the metal film for the reflector surface 90 of the SPR detector and the sensing surface for the semiconductor device may range from 80 nm to 125 nm.

In prior SPR sensors, approximately 10% of the metal film that provides the reflector surface 90 is in contact with the liquid solution 111 whilst the rest of the area is occupied by the cell holding the fluid. The optical spot size is typically smaller than metal film surface area. In some embodiments of the present disclosure consistent with FIGS. 7A and 8A, the extended gate FET sensor has a metal film (provided by the reflector surface 90) attached to the gate structure, wherein this metal film forms the sensing surface 112 for the FET biomolecule sensor. The embodiments depicted in FIGS. 7A and 8A require that substantially the entire area of the sensing surface 112 for the FET biomolecule sensor be in contact with the liquid solution 111 from which the measurement is taken. A method has been proposed that successfully combines both SPR & FET sensing methods such that the sensing surface, i.e., reflective surface 90, simultaneously meets the criteria for both techniques and provides unique information that would not be achieved through a single method, i.e., SPR or semiconductor biomolecule sensor individually.

SPR sensing provides information about refractive index change at/near the solid liquid interface in the liquid solution sample, wherein the refractive index can be directly correlated to mass of solute within the liquid solution with strong binding ligands. Sensing occurs throughout the entire evanescent wave, in which the evanescent wave is much larger than the dimension of biomolecules. In some embodiments, SPR provides the total mass and allows determination of surface coverage, while the semiconductor device sensing, e.g., FET or BJT sensor, provides information about the electrical environment. The semiconductor device sensing typically occurs within the Debye length, wherein the Debye length is smaller than the dimension of biomolecules in typical media used in liquid solution samples. The semiconductor device sensor, e.g., FET or BJT sensor, typically gives the local charge bound to the sensing surface, i.e., reflector surface 90.

Simultaneous SPR and semiconductor device sensors, e.g., FET and/or BJT sensors, can in principle provide complex information, such as molecular orientation at an interface (structure of bound species). Further, the presence of interfacial charge is known to influence kinetics of DNA binding and hybridization the latter of which can be correlated with base pair mismatch. This type of configuration could be useful for control & interpretation of molecular binding. Simultaneous detection by both SPR and semiconductor sensor methods results in higher detection accuracy & fewer false positives. Simultaneous measurement may include refractive index at the surface liquid solution sample by SPR, mass of the molecules in the at the interface by SPR and charges measured by the semiconductor sensor, e.g., FET sensor or BJT sensor, on charged target bio-molecules, e.g., proteins and DNA. Correlation of data provided by SPR and semiconductor sensors, e.g., FET sensor or BJT sensor, can provide insight into adsorption/desorption of biomolecules from the sensing surface, as well as changes in protein conformation or other charge target (e.g. DNA/RNA) configurations. Further, the simultaneous measurement can enable the measurement of changes in optical properties of the liquid solution sample at the interface as a function applied voltage to metal sensing surface of the semiconductor sensor, which is the reflective surface 90 of the SPR sensor.

FIG. 7A depicts one embodiment of a combined semiconductor device, e.g., biomolecule FET sensor, and surface plasmon resonance spectroscopy (SPR) based bio-sensor that employs a prism coupler 110. In this embodiment, the reflective surface 90 for the SPR sensor is smooth, as opposed to having a grating. In this embodiment, a reference electrode 400 is immersed in the liquid solution 111, and a voltage (Vg) is applied to it. The sensing signal for the FET 200 is measured by measuring the drain current (Id) flowing between source and drain in the threshold regime, where $|V_g|<V_T$, where $V_g$ is the gate voltage applied to gate electrode 209 and $V_T$ is the threshold voltage. When biomolecules attach to the sensing surface 112, i.e., reflective structure 90 of the SPR, charges on the molecules would cause the threshold voltage ($V_T$) to change, which in turn causes the sensing drain current to change. The sensing surface 112 of the FET sensor, which may also be the reflective surface 90 of the SPR, may be comprised of a metal film. In the embodiment that is depicted in FIG. 7A, the entire sensing area for the FET sensor should be in contact with liquid solution 111 being measured, and the metal film thickness should be less than 150 nm, e.g., approximately 50 nm.

Figure 9:
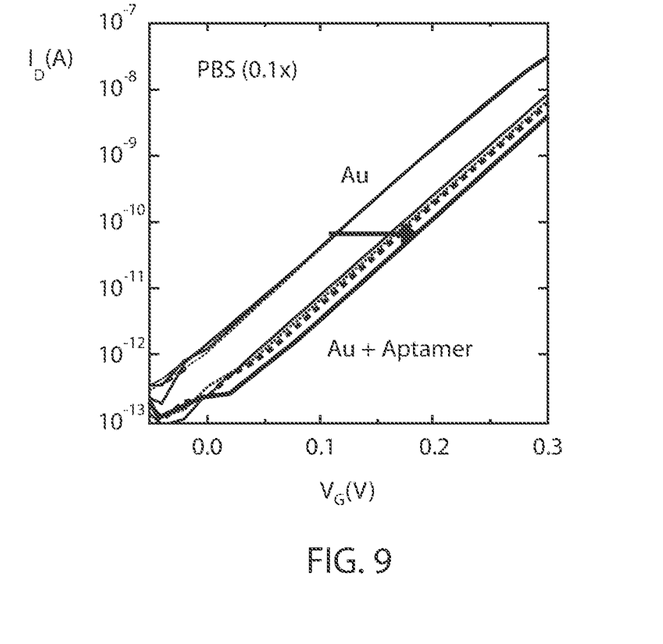
FIG. 9 is a plot of the drain current (Id) measured as a function of the gate voltage (Vg) taken from a field effect transistor (FET) biomolecule sensor in an arrangement with an SPR device as depicted in FIGS. 7A-8B, in accordance with the present disclosure.

Referring to FIG. 9, the optical spot size area 500 for taking the SPR measurements can be less than the sensing area 600 for the sensing surface of the semiconductor device, e.g., FET and/or BJT semiconductor device. There are many available choices for the metal of the sensing surface, which includes but are not limited to gold, silver, and copper. In some embodiments, the dimensions of the sensing surface should be less than the dimensions of the fluid cell but greater than the dimensions of the light source projected on the sensor surface.

FIG. 8A depicts one embodiment of a combined semiconductor device, e.g., biomolecule FET sensor, and surface plasmon resonance spectroscopy (SPR) based bio-sensor that employs a grating coupler. In the embodiment that is depicted in FIG. 8A, surface plasmons are coupled using a metallic grating. Grating coupled SPR may be employed with thicker films, e.g., gold films, for the reflective surface 90 than the embodiments of the present disclosure using prism coupling, as depicted in FIG. 7A. Similar to the embodiment that is described above with reference to FIG. 7A, a reference electrode 400 is immersed in the liquid solution 111, and a voltage (Vg) is applied to it. Sensing for the FET sensor depicted in FIG. 8A is similar to the previous configuration that is depicted in FIG. 7A.

Figure 10:
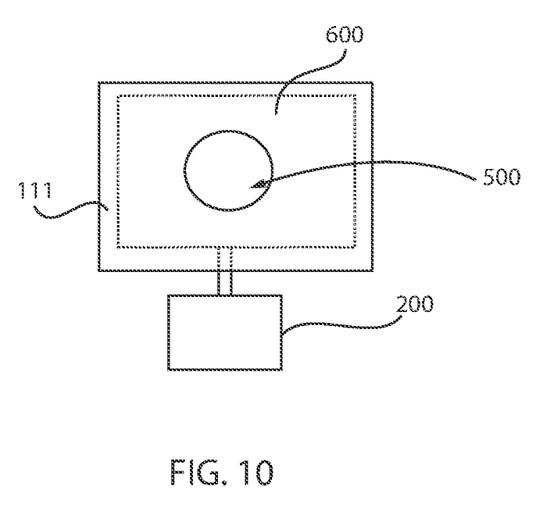
FIG. 10 is a top down view depicting a sensing surface for the combined SPR and semiconductor device biomolecule sensor that is depicted in FIGS. 7A-8B, in accordance with the present disclosure.

FIG. 10 is a plot of the drain current (Id) measured as a function of the gate voltage (Vg) taken from a field effect transistor (FET) biomolecule sensor in an arrangement with an SPR sensor as depicted in FIGS. 7A-8B. The FET sensor includes a gold surface as an extended gate which provides the sensing surface of the FET sensor for detecting aptamers. Drain current (Id) is measured as a function of gate voltage (Vg) applied to solution before and after the self-assembly of aptamers on the gold surface. As depicted in FIG. 10, the drain current (Id) curve shifts when aptamers (affinity linkers) are attached to the gold sensing surface, in which the detection shift is towards right indicating that aptamers are negatively charged. The aptamers are usually anchored to gold via thiol functionality. As more aptamers bind to the gold surface, the ID curves shift away from the curve corresponding to the bare gold surface.

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A sensor in electrical communication with a controller, the sensor comprising:
   a bipolar junction transistor including an emitter region, a base region, and a collector region;
   a reservoir containing a solution, the reservoir positioned adjacent the base region of the bipolar junction transistor; and
   a single metal containing contact directly contacting both the base region and the reservoir on opposed ends thereof.

2. The sensor of claim 1, wherein the metal containing contact provides a sensing surface for measuring at least one of presence of biomolecules in the solution, changing pH of the solution or a temperature of the solution.

3. The sensor of claim 2, wherein the emitter, base, and collector regions are arranged in a lateral orientation.

4. The sensor of claim 2, wherein the emitter, base, and collector regions are arranged in a vertical orientation.

5. The sensor of claim 2, wherein the metal containing contact includes titanium nitride (TiN), a conducting metal coated with a thin layer of silver chloride (AgCl), silicon dioxide and/or other insulators, gold (Au), silver (Ag) or a metal and semiconductor alloy that supports a surface plasmon wave.

6. The sensor of claim 2, wherein the metal containing contact has a silver chloride surface, and change in collector current indicates a change in chloride concentration in the solution, and changes in a subthreshold swing of the bipolar junction transistor indicates changes in the temperature of the solution.

7. The sensor of claim 2, wherein the metal containing contact includes titanium nitride (TiN), wherein the metal containing contact measures pH of the solution.

8. The sensor of claim 2, wherein a first dielectric spacer is formed on an interface between the emitter region and the base region to electrically isolate the emitter region from the collector region.

9. The sensor of claim 8, wherein a second dielectric spacer is formed on an interface between the base region and the collector region to electrically isolate the emitter region from the collector region.

10. The sensor of claim 2, wherein the bipolar junction transistor is programmed by the controller to measure change in charge density in proximity to the metal containing contact, which is correlated to a concentration of molecules of the solution contained within the reservoir.

11. The sensor of claim 10, wherein the concentration of molecules are simultaneously measured by the bipolar junction transistor and a surface plasmon resonance (SPR) detector.

12. A sensor in electrical communication with a controller, the sensor comprising:
   a bipolar junction transistor including an emitter region, a base region, and a collector region;
   a reservoir containing a solution, the reservoir positioned adjacent the base region of the bipolar junction transistor;
   a first metal containing contact extending from the base region into the reservoir;
   a second metal containing contact extending from the emitter region to a first metal stud; and
   a third metal containing contact extending from the collector region to a second metal stud.

13. The sensor of claim 12, wherein the first metal containing contact provides a sensing surface for measuring at least one of presence of biomolecules in the solution, changing pH of the solution or a temperature of the solution.

14. The sensor of claim 13, wherein the emitter, base, and collector regions are arranged in a lateral orientation.

15. The sensor of claim 13, wherein the emitter, base, and collector regions are arranged in a vertical orientation.

16. The sensor of claim 13, wherein the first metal containing contact includes titanium nitride (TiN), a conducting metal coated with a thin layer of silver chloride (AgCl), silicon dioxide and/or other insulators, gold (Au), silver (Ag) or a metal and semiconductor alloy that supports a surface plasmon wave.

17. The sensor of claim 13, wherein the first metal containing contact has a silver chloride surface, and change in collector current indicates a change in chloride concentration in the solution, and changes in a subthreshold swing of the bipolar junction transistor indicates changes in the temperature of the solution.

18. The sensor of claim 13, wherein the first metal containing contact includes titanium nitride (TiN), wherein the metal containing contact measures pH of the solution.

19. The sensor of claim 13, wherein a first dielectric spacer is formed on an interface between the emitter region and the base region to electrically isolate the emitter region from the collector region.

20. The sensor of claim 19, wherein a second dielectric spacer is formed on an interface between the base region and the collector region to electrically isolate the emitter region from the collector region.

* * * * *